US005733278A

United States Patent [19]

[11] Patent Number: 5,733,278
[45] Date of Patent: Mar. 31, 1998

Slatkine et al.

[54] METHOD AND APPARATUS FOR HAIR TRANSPLANTATION USING A SCANNING CONTINUOUS-WORKING $CO_2$ LASER

[75] Inventors: Michael Slatkine, Fairlawn; Douglass S. Mead, III, Allendale, both of N.J.; Eliezer Zair, Bnei-Brak, Israel

[73] Assignee: Laser Industries Limited, Tel Aviv, Israel

[21] Appl. No.: 346,878

[22] Filed: Nov. 30, 1994

[51] Int. Cl.[6] .......... A61B 17/36

[52] U.S. Cl. .......... 606/13; 606/9

[58] Field of Search .......... 606/9, 10, 11, 606/12, 15, 16, 17

[56] References Cited

U.S. PATENT DOCUMENTS

| | | | |
|---|---|---|---|
| 3,884,236 | 5/1975 | Krasnov | 128/303 |
| 4,144,876 | 3/1979 | DeLeo . | |
| 4,388,924 | 6/1983 | Weissman et al. . | |
| 4,469,098 | 9/1984 | Davi | 128/303.1 |
| 4,566,453 | 1/1986 | Kumano et al. | 128/303.1 |
| 4,587,396 | 5/1986 | Rubin | 219/121 LU |
| 4,672,969 | 6/1987 | Dew | 128/397 |
| 4,718,418 | 1/1988 | L'Esperance, Jr. | 606/4 |
| 4,733,660 | 3/1988 | Itzkan | 128/303.1 |
| 4,768,517 | 9/1988 | Joachim . | |
| 4,812,613 | 3/1989 | Gorisch | 606/11 |
| 4,887,019 | 12/1989 | Reis et al. | 606/4 |
| 4,917,083 | 4/1990 | Harrington et al. | 606/15 |
| 5,071,417 | 12/1991 | Sinofsky | 606/8 |
| 5,123,028 | 6/1992 | Hobart et al. . | |
| 5,137,533 | 8/1992 | Giampapa . | |
| 5,280,378 | 1/1994 | Lombardo . | |
| 5,360,447 | 11/1994 | Koop | 623/15 |
| 5,397,327 | 3/1995 | Koop et al. | 606/17 |
| 5,411,502 | 5/1995 | Zair | 606/10 |

FOREIGN PATENT DOCUMENTS

| | | |
|---|---|---|
| 0243593B1 | 2/1987 | European Pat. Off. . |
| WO88/00814 | 2/1988 | WIPO . |

OTHER PUBLICATIONS

Dzubow, L., Hair Transplantation Process and Product, J. Derm. Surg. Oncology vol. 20, No. 8, Aug. 1994, pp. 509–510.

Unger, W.P. and David, L.M., Laser Hair Transplantation, J. Derm. Surg. and Oncology vol. 20, No. 8, Aug. 1994 pp. 515–521.

*Primary Examiner*—Angela D. Sykes
*Assistant Examiner*—Sonya Harris-Ogugua
*Attorney, Agent, or Firm*—Cobrin Gittes & Samuel

[57] ABSTRACT

A method and apparatus for laser-assisted hair transplantation preferably utilizes a CW mode $CO_2$ laser, which may already have been installed in a surgeon's office, and a flashscanner to scan the laser over the area of holes to be drilled, thereby minimizing thermal necrosis on the recipient walls or slits. Optionally, a computer controls the laser/flashscanner assembly to redirect the beam from hole to hole, so as to rapidly drill a plurality of uniformly spaced holes. Advantageously, the time duration of the laser procedure is not limited, but depends instead on the CW laser power level parameters and the focal length selected for the procedure, thereby affording the surgeon significant flexibility in choosing appropriate treatment parameters.

16 Claims, 6 Drawing Sheets

4
7
2
6
1
33
22
⊖Max.
5
9
8

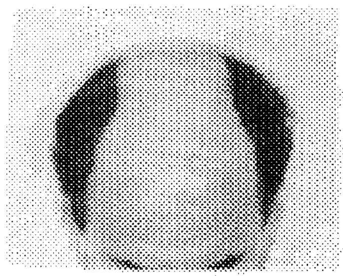
FIG.6A
FIG.6B
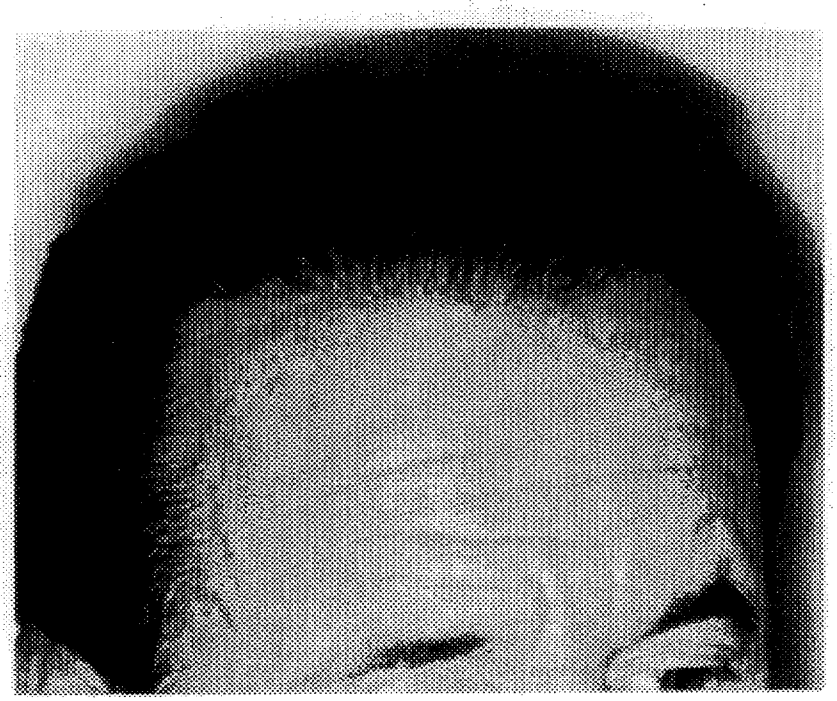
FIG.6C

METHOD AND APPARATUS FOR HAIR TRANSPLANTATION USING A SCANNING CONTINUOUS-WORKING $CO_2$ LASER

FIELD OF THE INVENTION

The present invention relates generally to laser devices and biomedical applications thereof. More specifically, the invention relates to laser-based methods and apparatus for performing dermatological procedures, such as hair transplantation.

CROSS-REFERENCE TO RELATED APPLICATION

The present application is related to U.S. patent application Ser. No. 08/175,980 (the "'980 application"), entitled SYSTEM FOR CAUSING ABLATION OF A TARGET MATERIAL OF LIVING TISSUE WHILE NOT CAUSING DAMAGE BELOW A PREDETERMINED DEPTH, filed Dec. 30, 1993, the disclosure of which is hereby incorporated herein by reference.

BACKGROUND OF THE INVENTION

Hair transplantation is a widely-performed procedure.

Typically, it involves implanting many individual grafts. The individual grafts may be single-follicle (so-called "micro") grafts or pair/multiple-follicle (so-called "mini") grafts. Each graft often requires that a hole of 0.8–1.4 mm diameter be drilled in the scalp. Traditionally, a single hair transplantation session involved drilling approximately 200–2500 holes using a polished drill (such as the Transhair Micro Driller) and implanting a graft in each hole.

Although hair transplantation is an office procedure, it is usually long (e.g., 3 hours) and tedious, due to excessive bleeding during the procedure and the need to individually drill each hole. Irregular skin surface is a common post-operative complication of traditional hair transplantation procedures.

One laser-assisted hair transplantation technique has been reported in U.S. Pat. No. 5,360,447, incorporated herein by reference. The '447 technique utilizes a high peak-power (i.e., 400 Watts) pulsed, non-scanned laser beam to drill holes in the scalp. This technique is less-than-perfect because it uses a "defocused" beam, the diameter of which equals the diameter of the hole to be drilled. At the periphery of the defocused beam, the power density is substantially reduced (as compared to the center), and thus the tissue along the edge of the hole will suffer significant charing, or thermal damage. Moreover, the '447 technique cannot be applied with a CW laser beam (i.e., 40 Watts), because of substantial damage to the peripheral tissue walls.

In view of the above, it is apparent that there is a need for improved hair transplantation procedures which can be performed more rapidly, with less bleeding and fewer post-operative complications. Moreover, there is a need for a device that will enable hair transplantation to be performed with a CW laser. Also, there is a need for a method and apparatus for performing hair transplantation using the many CW mode lasers already installed in surgeons' offices. The present invention, as described below, provides such an improved method and apparatus for hair transplantation.

SUMMARY OF THE INVENTION

One object of the present invention relates to a method and apparatus for performing an improved hair transplantation procedure.

Another object of the invention relates to a method and apparatus for performing hair transplantation or a like procedure using a $CO_2$ laser in the continuous-working ("CW") mode.

Still another object of the invention relates to a method and apparatus for drilling the holes need for hair transplantation and like procedures using a rapidly scanning ("flashscanning") laser.

Yet another object of the invention relates to a method and apparatus for drilling a plurality of holes in the scalp or other biological tissue without need for manual repositioning between the drilling of each hole.

In accordance with one aspect of the invention, an improved method of hair transplantation includes the step of drilling a hole in the scalp using a CW mode $CO_2$ laser scanned over the area of the hole to be drilled. Preferably, said scanning is performed in a spiral pattern, or in a Lissajou pattern, as described in the '980 application. Optionally, the area to be scanned (i.e., the location of the hole) is automatically controlled by a computer, thereby enabling the drilling of a plurality of holes in a very short time, without need for manual repositioning.

In accordance with another aspect of the invention, an apparatus for performing an improved hair transplantation or like procedure includes a CW mode laser (preferably a $CO_2$ laser) and a flashscanner for directing a beam from said laser to scan the area of a hole to be drilled in a patient's scalp or like biological tissue. The flashscanner preferably includes one or more computer-controlled beam-deflecting mirrors. The mirrors are preferably controlled to scan the beam in a spiral pattern at a constant scanning velocity. Optionally, the flashscanner is programmed to relocate the area to be scanned by the laser beam, thus permitting multiple holes to be drilled in the scalp or other tissue without need for manual repositioning of the apparatus.

BRIEF DESCRIPTION OF THE DRAWINGS

The above, as well as other objects, features and advantages of the invention, are described in detail below, which description is indented to be read in conjunction with the following set of drawings, in which.

FIG. **4*a*** depicts a scalp with 2800 holes drilled by the flashscanner operating in conjunction with a CW mode $CO_2$ laser in accordance with the invention;

FIG. **4*b* depicts a scalp one day following the improved hair transplantation procedure of the invention; and FIGS. 5A, 5B and 5C and FIGS. 6A, 6B and 6**C depict exemplary pre-operative and post-operative (i.e., 4 month follow up) results of the improved hair transplantation procedure of the invention.

The file of this patent contains at least one photograph executed in color. Copies of this patent with color drawing (s) will be provided by the Patent and Trademark Office upon request and payment of the necessary fee.

DETAILED DESCRIPTION OF THE INVENTION

Figure 1:
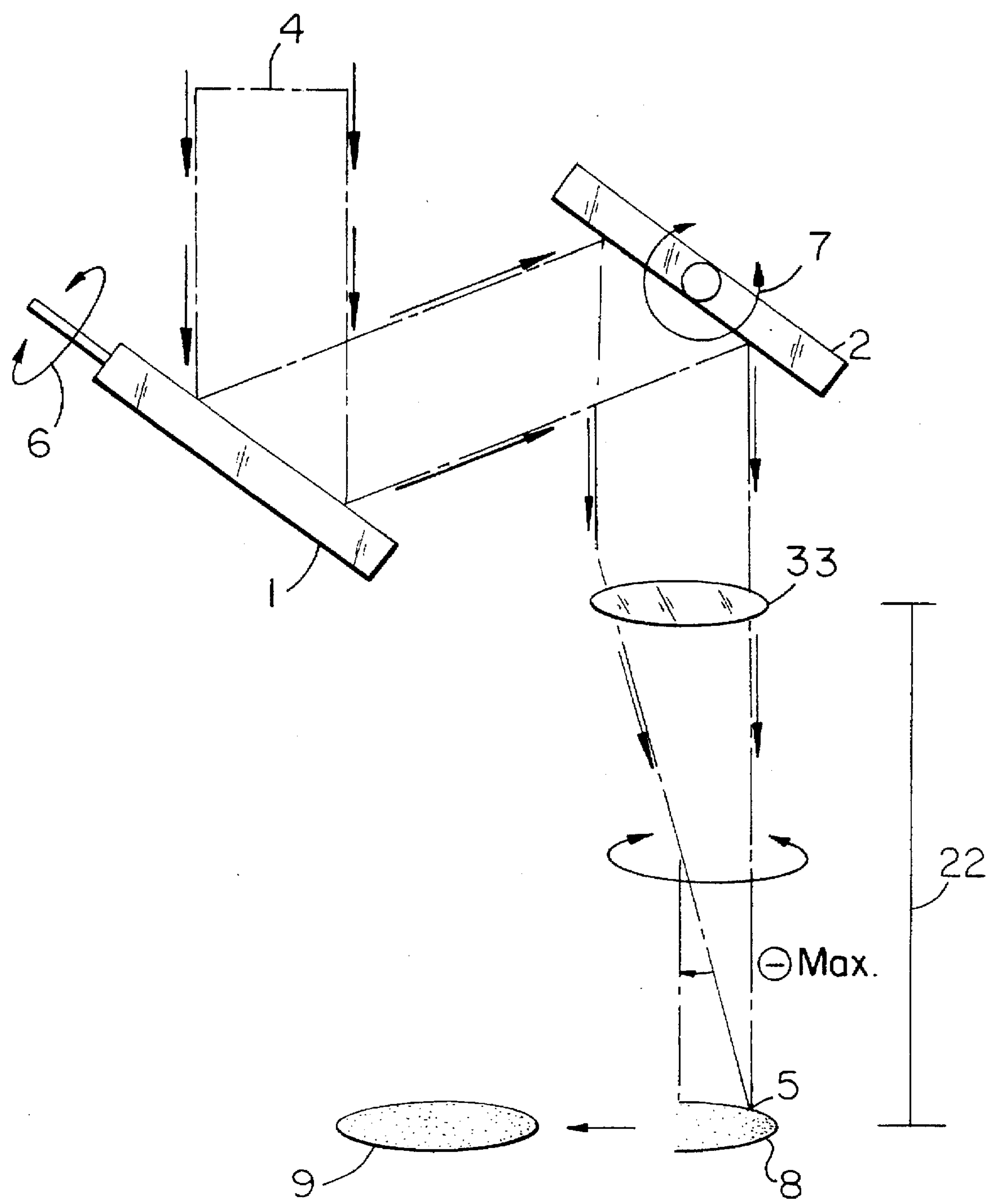
FIG. 1 illustrates the operation of a spiral flashscanner.

Referring to FIG. 1, a flashscanner 10 illustratively comprises first and second computer-controlled beam-deflecting mirrors 1 and 2, respectively, and a beam-focusing lens 3. A beam 4 from a CW mode $CO_2$ laser (not shown) is deflected by mirrors 1 and 2, and focused by lens 3 into a spot 5. (An alternative flashscanner, which scans a Lissajou pattern, is described in the '980 application. While the '980 application is directed to applications in which very thin tissue layers are char-free ablated, those skilled in the art will, in light of the disclosure herein, recognize that the apparatus disclosed in the '980 application can be adapted to perform the drilling steps involved in hair transplantation procedures.)

Beam-deflecting mirrors 1 and 2 are positioned nearly parallel, and are vibrated about axes 6 and 7, respectively, to direct spot 5 to scan a target area 8. The vibrational pattern of mirrors 1 and 2 is computer-controlled, so as to ensure a constant scanning velocity. Through control of the beam power, scanning rate and spot size, appropriate parameters for hair transplantation can be achieved. Preferred parameters are described below.

Also, by computer-controlled repositioning of mirrors 1 and 2, spot 5 can be moved to scan another target area 9. Such computer-controlled retargeting does not require manual repositioning of flashscanner 10. Thus, a plurality of uniformly spaced holes can be drilled very efficiently.

Figure 2:
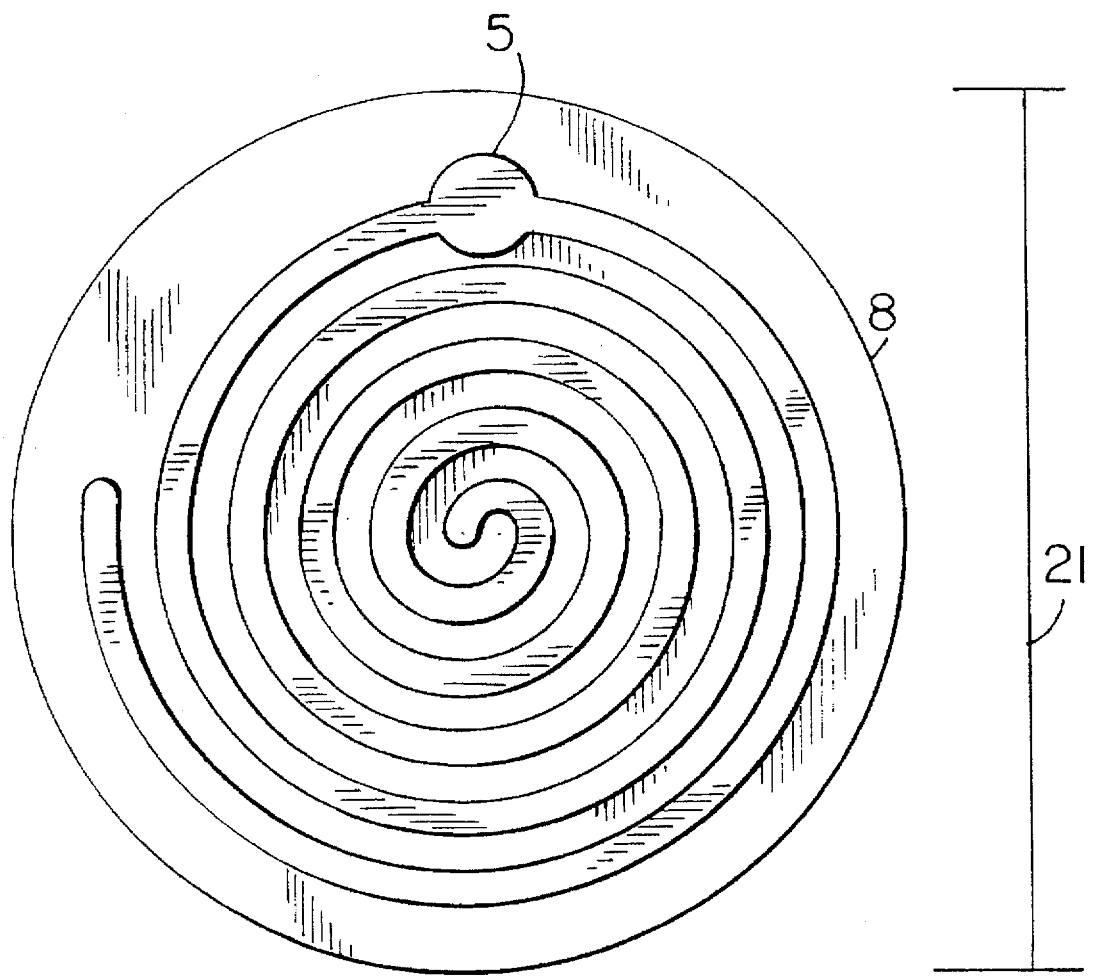
FIG. 2 depicts an illustrative spiral scanning pattern generated by the flashscanner.

Referring now to FIG. 2, spot 5 is preferably scanned in a spiral pattern 20 (preferably at constant velocity) to cover target area 8. In hair transplantation applications, spot 5 is focused at a focal length 22 of 80 mm (see FIG. 1*a*) to generate a spot size of 0.2 mm or less. Utilizing spiral scanning, target areas of 0.8, 1.2 and 1.4 mm in diameter 21 can be scanned for micro/mini graft applications. However, other power levels and time durations are possible, as will be appreciated by those skilled art.

With a typical laser power level of 30–40 Watts, the optical power is considerably higher than the threshold for vaporization of tissue without char, which is approximately 50 $W/mm^2$. Lack of char assures minimal thermal necrosis on the walls (of about 50 microns), thus ensuring excellent capability to later feed the hair grafts by internal oozing through the walls. In typical hair transplant applications, scanning a single target area takes about 0.2 seconds, and generates a clean char-free hole about 3–7 mm deep.

TABLE 1

| PREFERRED FLASHSCANNER SPECIFICATIONS | |
|---|---|
| Focal length | 80 mm |
| Scanning diameters | 0.8–1.6 mm |
| Scanning duration | 0.2 sec |
| Spot size | 0.15 mm |
| Instantaneous Dwelling Time | 1 ms |
| Scanning pattern | Spiral (constant velocity) |

Figure 3:
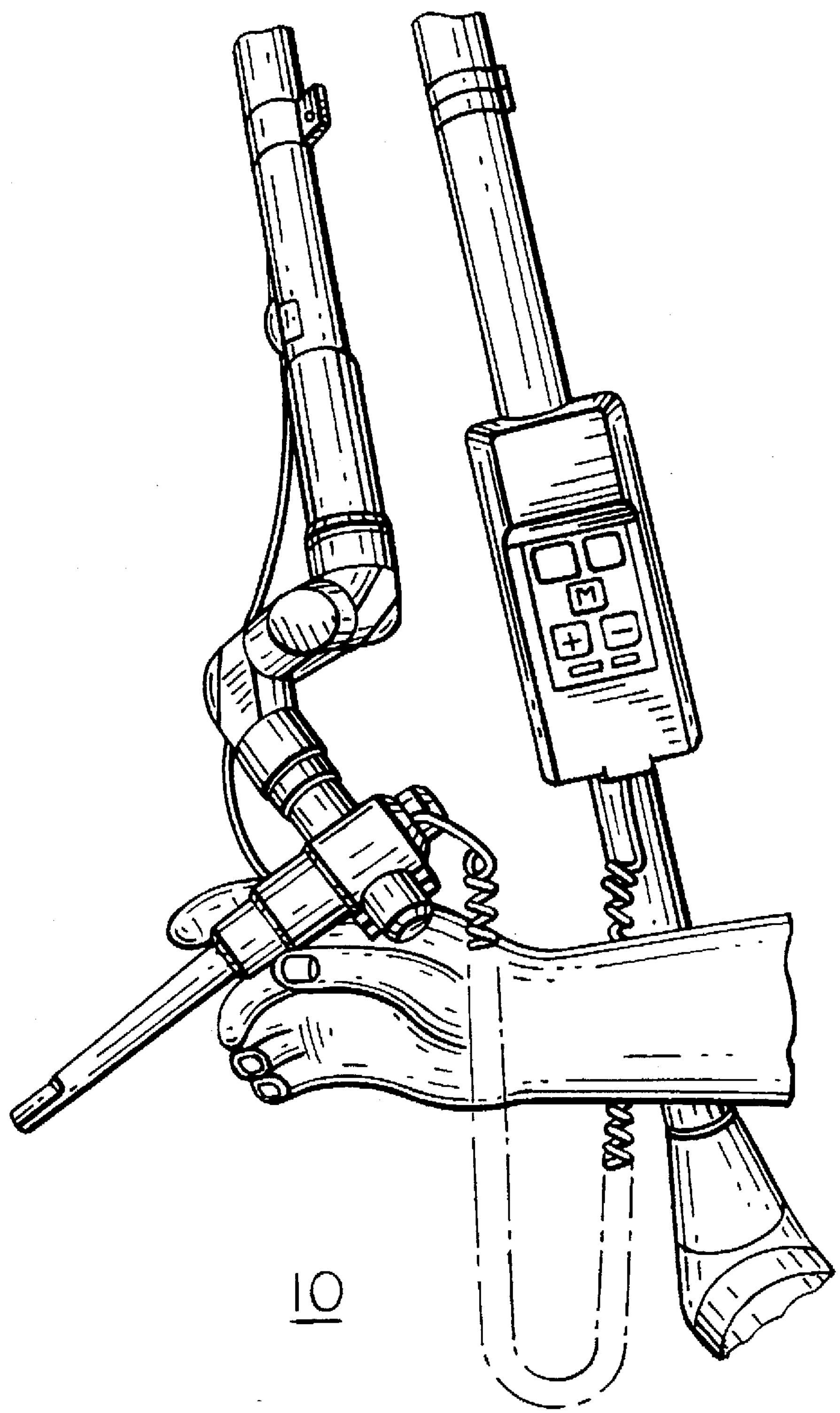
FIG. 3 depicts the exterior appearance of the flashscanner.

Referring to FIG. 3, flashscanner 10 preferably comprises a hand-held unit.

TABLE 2

PREFERRED TREATMENT PARAMETERS

| LOCATION | SCANNING DIAMETER | LASER POWER LEVEL | SINGLE HOLE SCANNING DURATION |
|---|---|---|---|
| First Line | 1.0 mm | 40 W | 0.1 sec |
| Front Head | 1.2 mm | 36 W | 0.2 sec |
| Back Head | 1.4 mm | 36 W | 0.25 sec |

PREFERRED OPERATING TECHNIQUE

In accordance with the invention, a laser-assisted hair transplantation procedure preferably begins by following the same steps performed in conventional, non-laser, hair transplantation: (1) preparing a donor strip using the conventional method with a scalpel, or using a well focused $CO_2$ laser beam; (2) preparing follicle grafts with a scalpel; and (3) subcutaneously injecting a local anesthetic (preferably 0.5% Xylocain with 1:100,000 Epinephrine).

Next, the $CO_2$ laser 31 is set to output a 40 Watt beam for a duration of 0.1 sec, and the flashscanner 10 is set to its smallest scanning diameter (approx. 0.8–1.0 mm). A single test hole is made to verity recipient hole depth in the first front line row. If necessary, the laser duration may be increased to 0.15 sec. Following the first line, the recipient hole diameters are increased to 1.2 mm in the front head. (see Table 2.) On the back of the head, the hole diameters are 1.4 mm. Once 5–7 mm hole depth has been confirmed, the entire drilling process of all holes is preferably completed before hair grafts are implanted. The field of view is constantly clear. For each hole, a few minutes after drilling, a minimal internal oozing can be observed, which is a sign that the follicle will be fed by diffusion of fluid and nutrients through the walls of the recipient holes.

Following the drilling process, the grafts are preferably simultaneously implanted by a few clinical assistants in "Megasesions," where over 2000 grafts may be implanted. Post-operative external bleeding does not occur because of wound contraction. After the operation, the patient's hair is washed aseptically and the patient is discharged.

EXEMPLARY RESULTS

To date, excellent results have been obtained with a CW laser on over 150 patients treated in accordance with the present invention. Graft numbers in excess of 2500 have been obtained. The excellent control of the laser beam and good site visibility enables easy implantation without affecting neighboring hair follicles or previously-transplanted hairs. Consequently, the present invention is also suitable for thickening operations for increasing hair density.

Figure 4A:
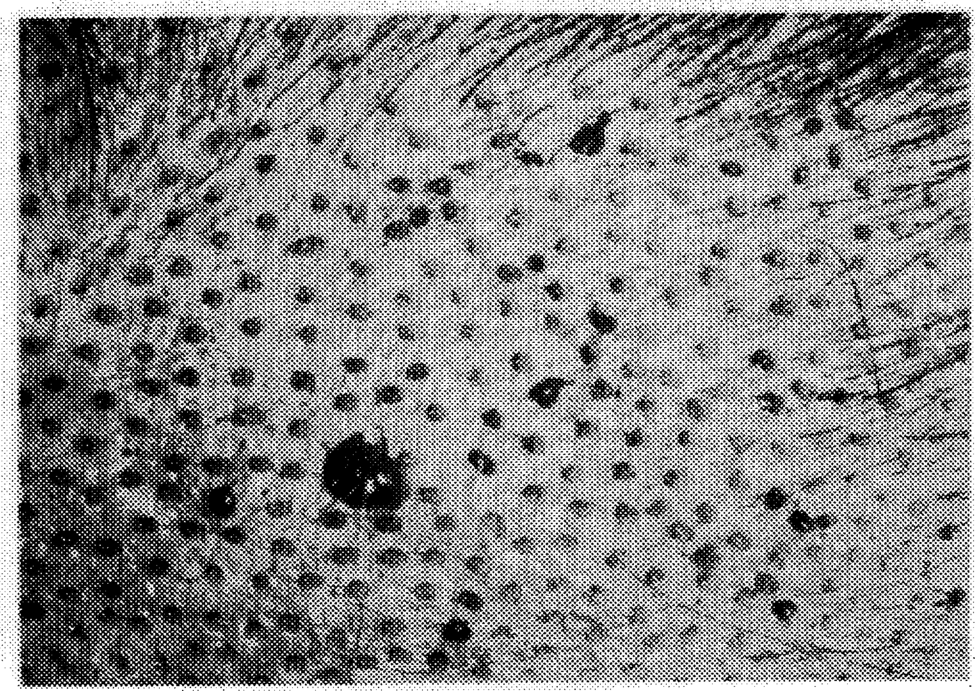

FIG. 4*a* depicts a scalp with 2800 holes drilled by the flashscanner operating in conjunction with a CW mode $CO_2$ laser. Note the uniformity of the holes and the lack of deepithelization around the holes.

Figure 4B:
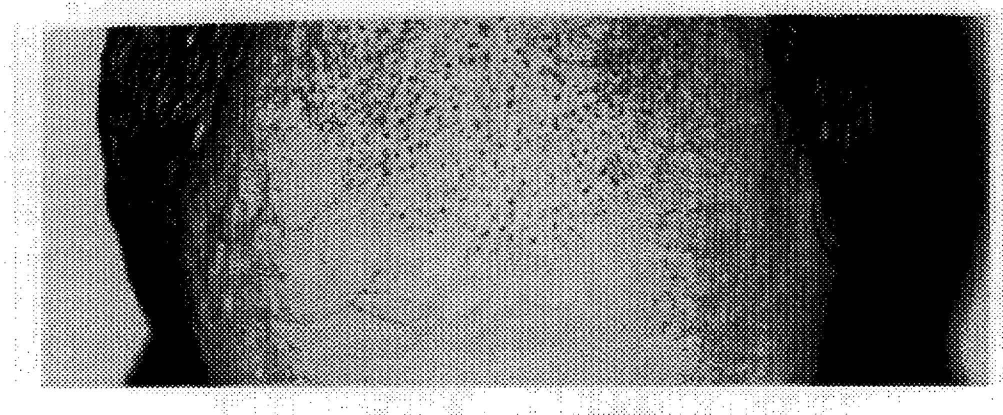
Figures 5A, 5B, 5C:
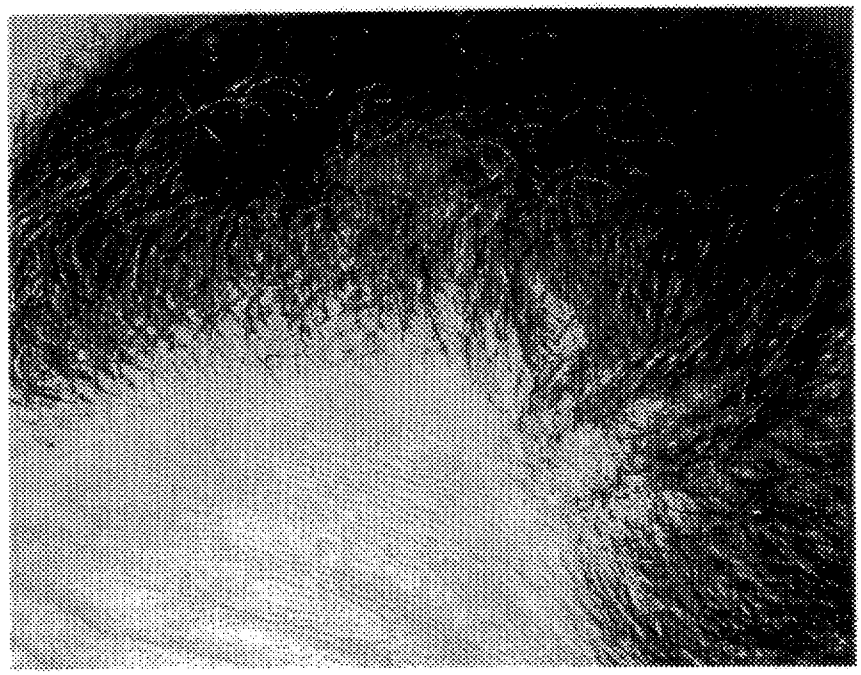

FIG. 4*b* depicts a scalp one day following the improved hair transplantation procedure of the invention. Notice the lack of deepithelization and the uniformity of the grafts.

FIGS. 5A, 5B and 5C and FIGS. 6A, 6B and 6C depict exemplary pre-operative and post-operative (i.e., 4 month follow up) results of the improved hair transplantation procedure of the invention. Hairs began to grow after 10 weeks. The number of implanted grafts (in FIG. 5) was 2800, implanted over two sessions.

What is claimed is:

1. A method of hair transplantation comprising:

providing a focused laser beam having a spot size;

scanning said beam continuously over a portion of a patient's scalp so as to create a hole having an area greater than at least three times said spot size; and implanting a graft having at least one hair follicle in said hole.

2. A method in accordance with claim 1 in which said scanning is in a predetermined pattern.

3. A method in accordance with claim 2 in which said pattern is a spiral.

4. A method in accordance with claim 1 in which said laser beam is provided by a $CO_2$ laser.

5. A method in accordance with claim 1 in which said scanning is for 0.2 sec.

6. A method in accordance with claim 5 in which said beam has a focal length of 80 mm.

7. A method in accordance with claim 1 in which said scanning is performed such that dwell time is at most 1 msec.

8. A method in accordance with claim 1 in which said scanning is performed over said area on a patient's scalp which is 0.8–1.6 mm diameter.

9. A method in accordance with claim 1 in which said laser beam is provided from a laser powered at 30 to 40 Watts.

10. A method in accordance with claim 1 in which said laser beam has a spot size of 0.15 mm.

11. A method in accordance with claim 1 in which said laser beam is scanned at a constant velocity.

12. A method in accordance with claim 1 in which a plurality of said areas on a patient's scalp are scanned.

13. A method of hair transplantation comprising:

providing a focused laser beam having a spot size;

scanning said beam sequentially and continuously over a portion of a patient's scalp so as to create a hole; and implanting a graft having at least one hair follicle in said hole.

14. A method of hair transplantation comprising:

providing a laser powered at 30–40 Watts;

providing a focused laser beam having a spot size by said laser;

scanning said beam continuously over a portion of a patient's scalp so as to create a hole; and implanting a graft having at least one hair follicle in said hole.

15. A method in accordance with claim 13 wherein the step of scanning is carried out in multiple passes to ablate said portion of said patient's scalp layer by layer.

16. A method in accordance with claim 14 wherein the step of scanning is carried out in multiple passes to ablate said portion of said patient's scalp layer by layer.

* * * * *